(12) United States Patent
Perot

(10) Patent No.: US 6,887,078 B2
(45) Date of Patent: May 3, 2005

(54) MODEL AND METHOD FOR TAKING A THREE-DIMENSIONAL IMPRESSION OF A DENTAL ARCH REGION

(75) Inventor: Jean-Marc Perot, Mount Royal (CA)

(73) Assignee: Cynovad Inc., Ville St-Laurent (CA)

( * ) Notice: Subject to any disclaimer, the term of this patent is extended or adjusted under 35 U.S.C. 154(b) by 0 days.

(21) Appl. No.: 10/203,646

(22) PCT Filed: Feb. 26, 2001

(86) PCT No.: PCT/FR01/00555

§ 371 (c)(1),
(2), (4) Date: Dec. 16, 2002

(87) PCT Pub. No.: WO01/64128

PCT Pub. Date: Sep. 7, 2001

(65) Prior Publication Data

US 2003/0124492 A1 Jul. 3, 2003

(51) Int. Cl.[7] .................................................. A61C 9/00
(52) U.S. Cl. ...................................................... 433/214
(58) Field of Search ........................... 433/34, 213, 223

(56) References Cited

U.S. PATENT DOCUMENTS

| 3,704,519 | A | | 12/1972 | Lystager |
| 4,363,625 | A | * | 12/1982 | der Avanessian ............ 433/74 |
| 4,767,331 | A | * | 8/1988 | Hoe ............................ 433/213 |
| 5,466,152 | A | | 11/1995 | Walter |
| 5,938,446 | A | | 8/1999 | Andersson et al. |
| 6,287,121 | B1 | * | 9/2001 | Guiot et al. ................. 433/218 |

FOREIGN PATENT DOCUMENTS

| EP | 0 913 130 A2 | 6/1999 |
| FR | 2.093.810 | 1/1972 |
| WO | WO 98/52491 | 11/1998 |

* cited by examiner

Primary Examiner—Cary E. O'Connor
(74) Attorney, Agent, or Firm—Alexandra Daoud; Ogilvy Renault

(57) ABSTRACT

A model for acquiring three dimensional data of a portion of a dental arch to receive a prosthesis, the model comprising a casting mold of a dental arch (2) mounted on a base (5), the portion of the casting mold to receive a prosthesis being separate from a remaining portion of the casting mold and mounted so as to be moveable and repositionable precisely on the base using pegs, wherein a mold of each tooth or portion of teeth adjacent to an extremity of the portion of the casting mold to receive the prosthesis (3) is also separate (6, 8, 9) from the remaining portion of the casting mold as well as from the portion of the casting mold to receive the prosthesis, and is mounted so as to be moveable and repositionable precisely on the base of the casting mold using pegs.

5 Claims, 2 Drawing Sheets

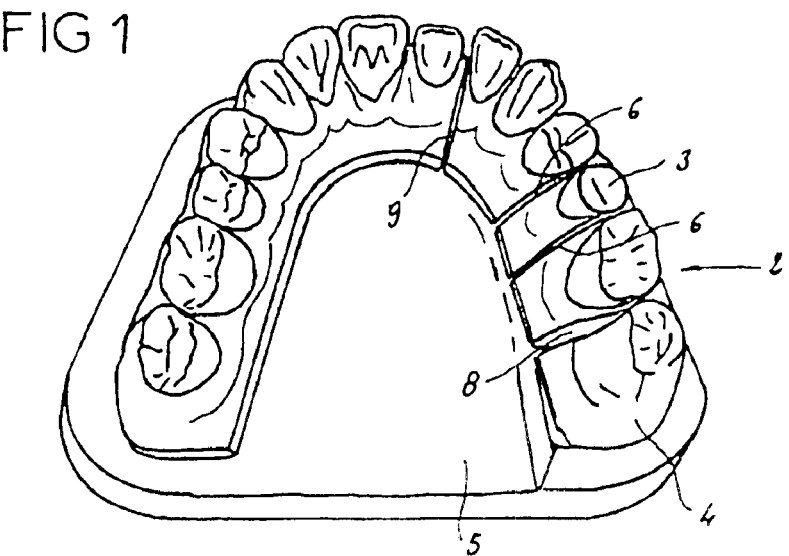
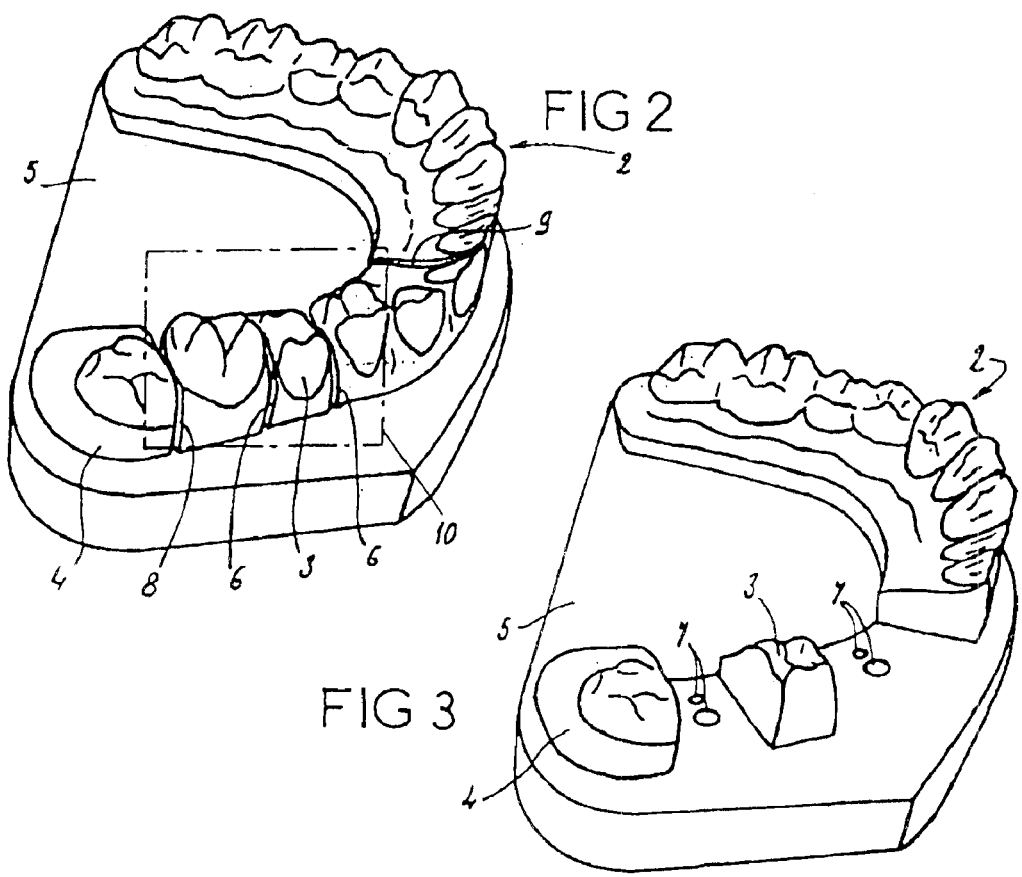

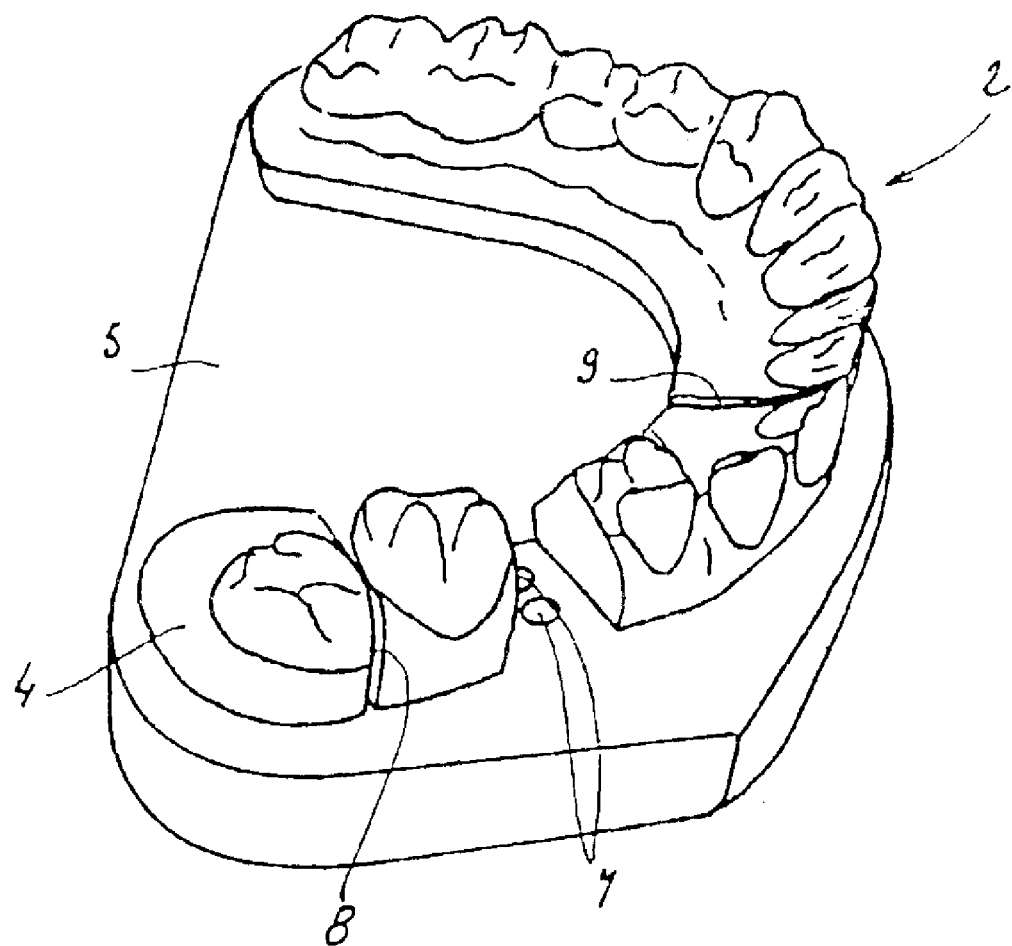

MODEL AND METHOD FOR TAKING A THREE-DIMENSIONAL IMPRESSION OF A DENTAL ARCH REGION

FIELD OF THE INVENTION

The invention relates to a dental model for acquiring three dimensional data of a portion of a dental arch destined to receive a prosthesis. More specifically, it relates to a dental model allowing the casting of a mold that is then digitized in order to calculate the shape and size of a prosthesis, wherein the prosthesis is then machined using a digital machine-tool system.

BACKGROUND OF THE INVENTION

In order to produce a dental prosthesis such as a crown or a bridge, a surgeon or dentist must first prepare the tooth or teeth that will serve as support for the prosthesis. This is done by milling and forming the tooth into a stump.

A casting mold is then made of either a part of the dental arch that will receive the prosthesis, or the entire dental arch, using a supple material. A casting mold is also made of the portion of or entire dental arch that is directly antagonistic to the area that is to receive the implant. Based on these casting molds, a technician can then reproduce a dental model representing the gums, the teeth, and the stumps by casting the mold in a plaster-like material. Protruding pegs included in the casting penetrate into a base. These pegs can be removed and replaced into the base.

The technician then proceeds to cut from the mold the portion that is to receive the prosthesis, consisting of one stump in the case of a crown and two stumps separated by a cavity in the case of a bridge. The cavity is made by sawing the platform of the casting mold in a substantially transversal direction to the arch.

Traditionally, the technician removes from the casting mold the portion of the dental arch that is to receive the prosthesis and builds the prosthesis on this portion. As the prosthesis is being built, it can be repositioned on the casting mold to ensure that the two correspond. The prosthesis is placed onto the casting mold and adjusted with respect to the neighbouring teeth, adjacent teeth, and the arches in general.

In the case of a prosthesis that is built using three dimensional data of a dental model acquired by a mechanical or optical sensor, the prosthesis shape and size is calculated using the three dimensional data before being machined. However, a problem arises when a casting mold must be made of areas that are not easily accessible by a mechanical or optical sensor. For example, areas located between teeth are hard to access. Therefore, it may be hard to obtain the actual shape of the surface of certain teeth that are facing stumps, or the shape of certain areas of the stumps or adjacent teeth.

SUMMARY OF THE INVENTION

Accordingly, an object of the present invention is to provide a dental model of a portion of a dental arch, as well as a method acquiring three-dimensional data of the dental model, wherein complete accessibility is ensured for all areas of a casting mold within the area receiving a prosthesis, and without additional work required by a technician in a prosthesis laboratory. The technique can be easily mastered by a technician in a prosthesis laboratory.

According to a first broad aspect of the present invention, there is provided a dental model comprising a casting mold of a dental arch mounted on a base, a portion of the casting mold to receive a prosthesis being separate from a remaining portion of the casting mold and mounted so as to be moveable and repositionable precisely on the base using pegs, wherein a mold of each tooth or portion of teeth adjacent to an extremity of the portion of the casting mold to receive the prosthesis is also separate from the remaining portion of the casting mold as well as from the portion of the casting mold to receive the prosthesis, and is mounted so as to be moveable and repositionable precisely on the base of the casting mold using pegs.

According to a preferred embodiment of the dental model, the separation of the portion of the casting mold that is to receive the prosthesis, as well as its adjacent portions, with respect to the rest of the casting mold is done by sawing in a substantially perpendicular manner the dental arch on which it resides, resulting in the separate portion having its own platform resting on the base of the remaining casting mold without adhering to it.

This model is used to acquire three dimensional data of the dental model with the use of either a mechanical sensor or an optical sensor. The measured results are then digitized before being subjected to a treatment allowing the contours of the prosthesis to be defined.

According to a second broad aspect of the invention, there is provided a method for acquiring three dimensional data of a dental model of a portion of a dental arch, the method comprising: positioning the model with respect to a system to acquire size and shape data of a portion of a dental arch that is to receive a prosthesis; identifying locations within the dental model wherein it is difficult to acquire shape and size data; removing from the dental model one of areas adjacent to the portion of the dental arch that is to receive the prosthesis and the portion of the dental arch that is to receive the prosthesis before acquiring size and shape data; and reconstructing the shape and size of the portion of the dental arch that is to receive the prosthesis based on acquired shape and size data.

A user begins by placing the dental arch into a measuring system. Inaccessible zones are then determined within the areas where data must be acquired.

According to a preferred embodiment, the method comprises acquiring a first set of data of the entire area of the dental arch, with a view to identify locations wherein acquiring data is difficult or impossible with the present state of the model.

Actually, determining the difficult areas can be done in a variety of ways. This can be done by a user that is knowledgeable of the limitations of the data acquiring system. It can be done by the data acquiring system using an automatic detection mechanism, such as a two-dimensional video or rapid pre-measuring in three dimensions. It can also be done by a user in combination with analysis methods incorporated into the data acquiring system.

Further to this analysis, the zones that are difficult or impossible to access are identified.

The method then comprises the step of determining a strategy for acquiring successive shapes, i.e. the order by which the different parts of the casting mold will be disassembled or separated from the model in order to acquire data.

The strategy can be determined in a variety of ways. It can be done by a user that is knowledgeable of the limitations of the data acquiring system. It can be done by the data acquiring system using an appropriate algorithm, or by a combination of a user and simulations incorporated into the data acquiring system.

The data is then acquired according to the strategy determined. By disassembling parts of the dental arch that result in an inaccessible zone, these zones can then be accessed and data acquired. The parts previously disassembled are then reassembled and the same principle is applied until all the necessary data has been acquired.

Therefore, the method according to the invention consists in manipulating the data acquiring system in order for it to: inform the user of an expected assembling or dissembling that must occur, suspend the acquisition of data to allow the disassembling process, re-acquire data after the piece has been disassembled, and reconstruct the shape of the entire portion of the arch for which data was acquired by combining data from each data acquisition performed.

BRIEF DESCRIPTION OF THE DRAWINGS

These and other features, aspects and advantages of the present invention will become better understood with regard to the following description and accompanying drawings wherein:

FIG. 1 is a top view of a dental model corresponding to part of a jaw;

FIG. 2 is a perspective view with a defined zone for which data is to be acquired;

FIGS. 3 and 4 are two perspective views respectively of different stages of data acquisition.

DETAILED DESCRIPTION OF THE PREFERRED EMBODIMENT

FIG. 1 represents a dental model of the jaw and comprises a casting mold 2 of a certain number of teeth, one of which is a stump 3 destined to receive a crown. The casting mold comprises a platform 4, which resides on a base 5. As shown in the figure, the portion of the casting mold comprising the stump 3 is separated from the adjacent portions by two slots 6 substantially transversal to the dental arch of the jaw. The platform 4 does not adhere to the base 5. It is therefore possible to remove the portion comprising the stump 3, as shown in FIG. 4, this portion being repositionable due to pegs (not shown) engaged in two holes 7 in the base. Such cuts, such as 8 and 9 respectively, are formed on the other side of a tooth adjacent to the stump 3 and located towards the back of the dental arch, and at the other extremity of a group of three teeth located towards the front of the dental arch. The two portions surrounded by the slots, 6 and 8 for one portion and 6 and 9 for the other portion, can be removed independently from each other and repositioned precisely using pegs, such as was described for the portion of the casting comprising the stump 3.

It can be appreciated from FIG. 2 that the zones between the stump and the two neighbouring teeth are very narrow, such that it is difficult, if not impossible, to acquire data correctly for the sides of the stump that are facing the two adjacent teeth, as well as the sides of the teeth that are facing the stump.

The zone where the data is to be acquired is first identified. This zone 10, is surrounded by a dotted line in FIG. 2. As shown in FIG. 3, parts are first disassembled from each area surrounding the stump 3, in order to acquire data corresponding to the shape of the stump, now completely accessible. The two surrounding areas are then reassembled, after which the stump 3 is removed from the model, as shown in FIG. 4. Data is then acquired for the size and shape of the adjacent teeth and the base, after which an algorithmic reconstruction is used to reproduce the entire model using data acquired for the entire zone 10, and the base 5 is eliminated.

This acquisition being done, it is now possible to proceed to the determination of the shape of the prosthesis that is to reside on the stump 3.

The invention is a great improvement on the existing techniques by providing a model that is simple in structure and in method of application, allowing three-dimensional data to be acquired for all parts of a dental model that is to receive a prosthesis. The method is performed while keeping with the rules of the art as they are commonly known in the field of dental prostheses.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. Process for tridimensional impression-taking of an arch area, characterized in that it consists in:
   providing a casting of at least the arch area intended to receive a prosthesis, the casting mounted on a stand;
   positioning the casting opposite a device for acquisition of a shape of the arch area intended to receive the prosthesis,
   identifying silts whose shape acquisition is difficult or impossible to carry out as is,
   effecting, according to said identifying, a removal of portions of the casting such that said sites are visible by said device for acquisition;
   carrying out at least one shape acquisition of said casting on said stand after said removal,
   and restoring the shape of the arch area whose shape must be obtained, from the different shape acquisitions that were carried out.

2. Process according to claim 1, characterized in that it consists in effecting a first acquisition of the entire area of the arch whose shape must be obtained, in order to identify sites whose shape acquisition is difficult or impossible to effect as is.

3. Process according to claim 2, characterized in that it then consists in determining a strategy of successive shape acquisitions, including an order in which different portions of the casting will be dismantled and in which different impression-taking will take place.

4. Process according to any one of claims 1 to 3, characterized in that it consists in guiding an impression-taking device in order that the latter:
   informs the user that a dismantling and/or a rebuilding of a portion of the arch are expected,
   delays an impression-taking to allow for a dismantling of an arch portion,
   take over the measurement after dismantling, and
   restore the shape of the arch area whose shape must be obtained, from the different shape acquisitions that were carried out.

5. Process according to claims 1, characterized in that said effecting a removal of portions of the casting comprises removing portions that are adjacent to the area intended to receive the prosthesis.

* * * * *

UNITED STATES PATENT AND TRADEMARK OFFICE
CERTIFICATE OF CORRECTION

PATENT NO.     : 6,887,078 B2
DATED          : May 3, 2005
INVENTOR(S)    : Jean-Marc Perot It is certified that error appears in the above-identified patent and that said Letters Patent is hereby corrected as shown below:

<u>Column 4,</u>
Line 31, please replace the word "silts" with the word -- sites --.

Signed and Sealed this

Ninth Day of August, 2005

JON W. DUDAS
*Director of the United States Patent and Trademark Office*